United States Patent [19]

Nagasaki et al.

[11] Patent Number: 4,663,657
[45] Date of Patent: May 5, 1987

[54] IMAGE PICKUP APPARATUS FOR ENDOSCOPES

[75] Inventors: Tatsuo Nagasaki, Musashino; Hiroyoshi Fujimori, Hachioji, both of Japan

[73] Assignee: Olympus Optical Company, Ltd., Japan

[21] Appl. No.: 645,309

[22] Filed: Aug. 29, 1984

[30] Foreign Application Priority Data

Sep. 5, 1983 [JP] Japan .................. 58-163596

[51] Int. Cl.[4] ............................................. H04N 7/18
[52] U.S. Cl. ........................................ 358/98; 128/6; 358/42
[58] Field of Search ...................... 358/98, 1, 213, 901, 358/42; 128/4–11, 633, 634; 362/16, 18, 293, 32

[56] References Cited

U.S. PATENT DOCUMENTS

| 3,456,641 | 7/1969 | Yokota et al. ........................ 128/4 |
| 3,499,107 | 3/1970 | Sheldon ............................. 358/98 X |
| 4,213,462 | 7/1980 | Sato ................................... 128/634 |
| 4,361,863 | 11/1982 | Hagner ........................... 352/293 X |
| 4,423,436 | 12/1983 | Kimura ................................ 358/98 |
| 4,475,539 | 10/1984 | Konomura ....................... 358/98 X |
| 4,517,976 | 5/1985 | Murakoshi et al. .............. 128/4 X |
| 4,546,379 | 10/1985 | Sarofeen et al. .................... 358/42 |

FOREIGN PATENT DOCUMENTS

| 0055428 | 5/1977 | Japan ..................................... 358/98 |
| 0089451 | 8/1978 | Japan ..................................... 358/98 |

OTHER PUBLICATIONS

Fukui et al; "Handy Endoscopic Color TV System Using New Chalnicon Pickup Tube"; Toshiba Review, #97, pp. 24–29, May, Jun. '75.

Primary Examiner—James J. Groody
Assistant Examiner—Victor R. Kostak
Attorney, Agent, or Firm—Ostrolenk, Faber, Gerb & Soffen

[57] ABSTRACT

An image pickup apparatus for endoscopes, which makes an image of an object to be observed employing a solid-state image pickup device such as a charge-coupled-device, is provided with an optical filter disposed on the optical path including an illumination optical system for applying illumination light to the object to be observed and an objective optical system for forming an optical image of the object to be observed on said solid-state image pickup device, for correcting the spectral properties of said optical path, thereby permitting a faithful color picture image to be reproduced and a picture image suitable for a kind of the object to be observed to be made.

5 Claims, 3 Drawing Figures

IMAGE PICKUP APPARATUS FOR ENDOSCOPES

BACKGROUND OF THE INVENTION

The present invention relates to an image pickup apparatus for an endoscope, and more particularly, to an apparatus for producing an image of an object to be observed under illumination of light emitted from an illumination optical system of the endoscope employing a solid-state image pickup device.

In recent years, an electronic type endoscope which produces an image of an object to be observed employing a solid-state image pickup device and displays the image of the object on a display apparatus such as a Brown tube has been brought into practical use.

The known solid-state image pickup device adapted to be used in an endoscope include charge transfer device such as a charge coupled device (CCD), a bucket brigade device (BBD) and a charge priming device (CPD), a static induction transistor (SIT) type and a metal oxide semiconductor (MOS) type.

Among the advantages of electronic type endoscope employing a solid-state image pickup device are that they make it easy to record an image of an object to be observed and are small (and will be miniaturized increasingly in future due to advances in high integration techniques) in comparison with an endoscope in which an optical image is formed on a fiber bundle for guiding an optical image. However, when the solid-state image pickup device is employed, it is necessary to form a color image.

A white color illumination lamp generally in use radiates more energy in an infrared ray wavelength zone than in a visual ray wavelength zone and the spectral properties of an illumination optical system and an image pickup optical system including all elements such as a lens system, a light guide and a solid-state image pickup device are not uniform so that it is difficult to reproduce a faithful color image. In addition, it is necessary to detect a difference in color tones in order to discriminate between an affected part and a normal part in a coeliac cavity. It is known that when an inspection is made with an endoscope the clear contrast has been formed by arranging a color filter of the blue group in an eyepiece portion of the endoscope. For example, it is possible to detect a small cancer.

SUMMARY OF THE INVENTION

It is an object of the present invention to provide an image pickup apparatus for an endoscope which is capable of reproducing a faithful color image by correcting the spectral properties of an optical path including an illumination optical system and an image pickup optical system in a uniform manner and of making a clear image by employing illumination light having the color tones suitable for an object to be observed.

According to the present invention, an image pickup apparatus for an endoscope employing a solid-state image pickup device is constructed such that an optical filter or filters for correcting the spectral properties of the overall optical path in both of an illumination optical system and an image pickup optical system or an optical filter or filters having the color tones suitable for an object to be observed are disposed in the optical path of at least one of the illumination optical system and the image pickup optical system, thereby permitting to reproduce a faithful image or to make a clear image.

According to the present invention, an image pickup apparatus for an endoscope having a solid-state image pickup device is effective in reproducing a faithful color image of an object to be observed since an optical filter or filters for correcting the spectral properties of the overall optical path including an illumination optical system and an image pickup optical system are disposed on the optical path of at least one of the illumination optical system and the image pickup optical system. Alternatively, the apparatus is effective in making a clear image since an optical filter or filters having the color tones suitable for the object to be observed are disposed to obtain proper illumination light.

DESCRIPTION OF THE PREFERRED EMBODIMENTS

Figure 1:
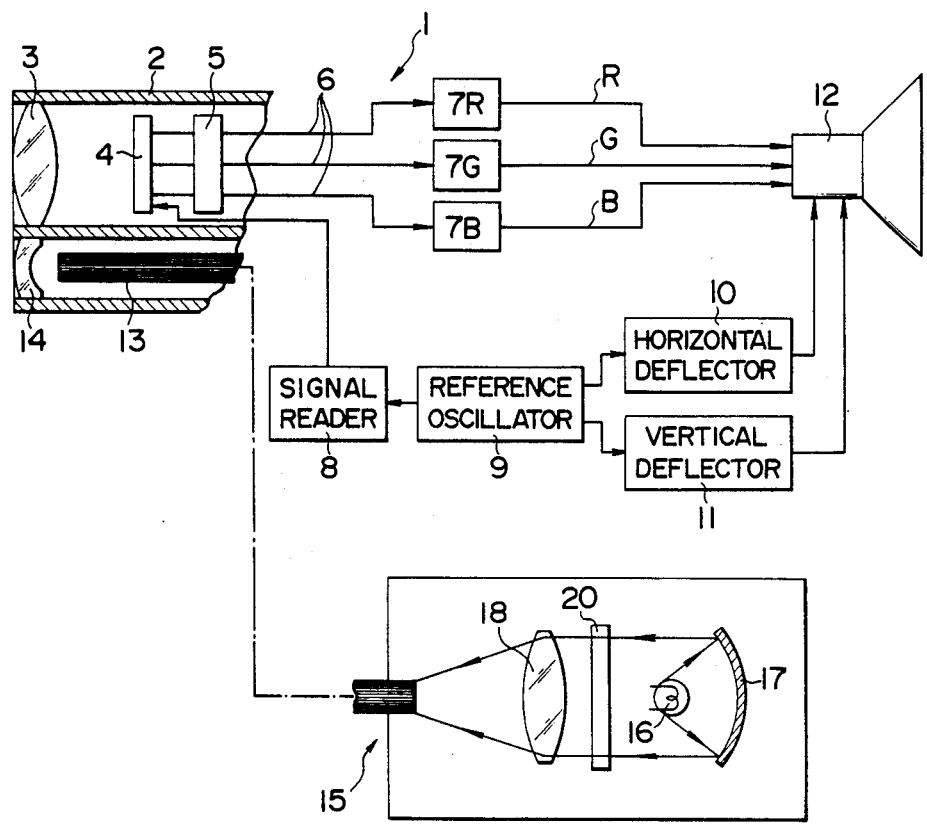
FIG. 1 is a schematic diagram illustrating an an embodiment of an image pickup apparatus for endoscopes according to the present invention.

Referring now to FIG. 1, an endoscope 1 includes an objective optical system 3 for image formation which is housed within the distal end portion of a slender insertion portion 2 and a solid-state image pickup device 4 which is made of a charge coupled device (CCD) and is disposed at the image forming position of the objective optical system 3 in such a manner that the image pickup plane of the pickup device 4 faces the objective optical system 3. A mosaic-like optical filter for the three primary colors (not shown), through which each color-wavelength light alone is allowed to transmit, is mounted on the image pickup plane of the image pickup device 4 so that a signal corresponding to each of picture elements, which signal is transmitted through the filter for transmitting three color light of red, green and blue, sequentially developed from three output terminals, for example, by a clock signal applied to the image pickup device 4. The developed signals are amplified by a preamplifier 5 having a low noise factor and are further amplified sufficiently by color amplifiers 7R, 7G and 7B in the rear stage through signal cables 6.

The clock signal which is applied to the image pickup device 4 in order to read a signal corresponding to each of the picture elements is produced from a signal reader 8. The clock signal is formed by a reference signal from a reference oscillator 9.

The reference signal is applied to a horizontal deflector 10 and a vertical deflector 11 to form horizontal and a vertical deflection signals, respectively, which are applied to the X and Y deflection terminals of a color Brown tube 12.

Color signals R, G and B of red, green and blue which are produced from the color amplifiers 7R, 7G and 7B are displayed on the color Brown tube 12 while being swept.

A light guide 13 made of a fiber bundle for transmitting illumination light is inserted into the insertion portion 2 of the endoscope 1. The distal (front) end of the light guide 13 is secured to the distal end inner wall of the insertion portion 2. An illumination window in front of the distal end of the light guide 13 is covered with a light distribution lens 14. The rear end of the light guide 13 is detachably mounted on a light source 15 through a light guide cable extending from the rear end of the insertion portion 2.

A white color illumination lamp 16 is disposed within the light source 15. Illumination light from the lamp 16 is reflected by a concave reflecting mirror 17 to form a substantially parallel light beam. The light beam is further converged to illuminate the rear end plane (incident plane) of the light guide 13.

An optical filter for correction 20 is disposed on the optical path between the lamp 16 and a condenser lens 18. The purpose of filter 20 is to give weight to the spectral properties of the illumination light in order to correct the spectral image pickup properties of the whole optical path including the illuminating optical system comprising lamp 16, condenser lens 18, light guide cable and light distribution lens 14 and the image pickup optical system comprising objective optical system 3 and solid-state image pickup device 4. Alternatively, a color filter suitable for a particular object to be observed is employed as the filter 20. For example, a color filter of the blue group is employed in the case of discriminating between an affected part and a normal part in a coeliac cavity.

With the image pickup apparatus for endoscopes of the structure according to the foregoing embodiment, it is possible to reproduce a faithful color image since the optical filter 20 for correcting the spectral image pickup properties of the whole optical path including the illuminating optical system from the lamp 16 through the object to be observed to the image pickup device 4 and the image pickup optical system is interposed between the lamp 16 and the condenser lens 18. Alternatively, when a color filter suitable for a particular object to be observed is employed, it is possible to make a clear image of the object to be observed. For example, when a color filter of the blue group is used for inspection of a coeliac cavity, it is possible to easily discriminate between an affected part and a normal part.

Figure 2:
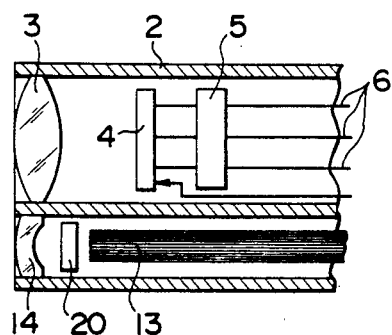
FIGS. 2 and 3 are sectional views of the essential parts of respective other embodiments of an image pickup apparatus for endoscopes according to the present invention.

In FIG. 2, which illustrates a second embodiment of the present invention, an image pickup apparatus for an endoscope is provided with an optical filter 20 for correction which is similar to that in the first embodiment, which is interposed between the distal (front) end of a light guide 13 in an insertion portion 2 and a light distribution lens 14. The others are similar to parts in the first embodiment.

The image pickup apparatus thus constructed has the same actions and effects as in the first embodiment.

Figure 3:
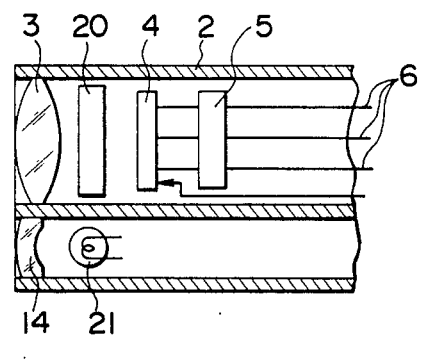

In FIG. 3, which illustrates a third embodiment of the present invention, an image pickup apparatus employs a midget lamp 21 (or a plurality of midget lamps when the amount of illumination light is insufficient) in place of the light guide 13 in the second embodiment shown in FIG. 2. The lamp 21 is disposed in face of the light distribution lens 14 within the insertion portion 2. An optical filter 20 for correction which is similar to that in the first and second embodiments is interposed between an objective optical system 3 and a solid-state image pickup device 4. It is to be noted that a (high brightness) light emission diode may be used in place of the midget lamp 21.

The image pickup apparatus constructed as just described has the same actions and effects as in the first embodiment.

Each of a foregoing embodiments is of the system employing a mosaic-like three primary color filter in a single solid-state image pickup device. It is to be noted that a system employing three separate solid-state image pickup devices responsive to respective three primary color images of red, green and blue into which an image of an object to be observed is decomposed or a system that sequentially develops three primary color component picture images from a single solid-state image pickup device, for example, by rotating three color filters of red, green and blue at a predetermined rotational speed on the part of the light source, may be employed. Specifically, the object of the present invention will be accomplished when an optical filter for correction is disposed at any point in the optical path from a light source through an object to be observed to a solid-state image pickup element. Furthermore, the optical filter may be of the weighted spectral properties of red, green and blue or of such nature that the spectral properties are correctable with regard to any one of red, green and blue or a combination of two or more thereof. Alternatively, a plurality of optical filters may be arranged in a plurality of positions. In addition, while the illumination optical system and the image pickup optical system are formed in a unitary manner in the foregoing embodiments, both may be formed separately.

What is claimed is:

1. An image pickup apparatus for an endoscope having an insertion portion to be inserted into an object to be observed, said image pickup apparatus, comprising:
   an illumination optical system including a source of illumination light and means for transmitting said illuminating light along a first optical path to an object being observed;
   an image pickup optical system for producing a color image of said object being observed, said image pickup optical system including a solid-state image pickup device and means for transmitting illuminating light reflected off said object to be observed along a second optical path to said solid-state image pickup device; and
   optical filter means for correcting spectral image pickup properties of an overall optical path which includes said first and second optical paths, said optical filter means being located in at least one of said first and second optical paths, said optical filter means giving weight to the spectral properties of elements constituting both said illumination optical system and said image pickup optical system in a manner which corrects the spectral properties of an illumination light incident upon said solid-state image pickup device in a uniform manner in a visual ray wavelength spectral zone so as to ensure that said image pickup optical system produces a faithful color image of said object to be observed.

2. An image pickup apparatus according to claim 1, in which said optical filter means is disposed in the optical path between an illumination lamp and a condenser lens, both being arranged within a light source apparatus associated with said endoscope.

3. An image pickup apparatus according to claim 1, in which said optical filter means is disposed in the first optical path between a light exit end plane of a light guide and a light distribution lens, both being arranged within said insertion portion of the endoscope.

4. An image pickup apparatus according to claim 1, also comprising an objective optical system disposed in said second optical path; said optical filter means being disposed in the second optical path between said objective optical system and said solid-state image pickup device, both being arranged within said insertion portion of the endoscope.

5. An image pickup apparatus according to claim 1, in which said solid-state image pickup device is one of a charge transfer device such as a charge coupled device, a bucket brigade device and a charge priming device, a static induction transistor and a metal oxide semiconductor.

* * * * *